United States Patent

Bremer et al.

(10) Patent No.: US 7,845,228 B2
(45) Date of Patent: Dec. 7, 2010

(54) ACTIVITY MONITORING

(75) Inventors: Joannes Gregorius Bremer, Eindhoven (NL); Paraskevas Dunias, Eindhoven (NL); Gillian Antoinette Mimnagh-Kelleher, Eindhoven (NL); Adrianus Petrus Johanna Maria Rommers, Eindhoven (NL); Wilhelmus Lambertus Marinus Cornelius Verhoeven, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1053 days.

(21) Appl. No.: 10/537,878

(22) PCT Filed: Nov. 21, 2003

(86) PCT No.: PCT/IB03/05336

§ 371 (c)(1),
(2), (4) Date: Jun. 7, 2005

(87) PCT Pub. No.: WO2004/052203

PCT Pub. Date: Jun. 24, 2004

(65) Prior Publication Data

US 2006/0075816 A1    Apr. 13, 2006

(30) Foreign Application Priority Data

Dec. 10, 2002   (EP)   .................................. 02080215

(51) Int. Cl.
    *G01P 3/04*   (2006.01)
(52) U.S. Cl. ........................ 73/510; 73/865.1; 73/865.3; 73/865.4; 340/669
(58) Field of Classification Search ............. 73/510, 73/514.34, 865.1, 865.3, 1.01; 235/116; 600/595
See application file for complete search history.

(56) References Cited

U.S. PATENT DOCUMENTS

| 5,125,412 | A | * | 6/1992 | Thornton | 128/670 |
|---|---|---|---|---|---|
| 5,317,304 | A | * | 5/1994 | Choi | 340/571 |
| 5,573,013 | A | * | 11/1996 | Conlan | 600/595 |
| 5,748,084 | A | * | 5/1998 | Isikoff | 340/568.1 |
| 5,760,690 | A | * | 6/1998 | French | 340/571 |
| 5,762,072 | A | * | 6/1998 | Conlan et al. | 600/595 |
| 5,869,760 | A | * | 2/1999 | Geen | 73/504.12 |
| 5,899,963 | A | * | 5/1999 | Hutchings | 702/145 |
| 6,122,960 | A | * | 9/2000 | Hutchings et al. | 73/493 |
| 6,148,280 | A | * | 11/2000 | Kramer | 702/153 |
| 6,201,476 | B1 | * | 3/2001 | Depeursinge et al. | 340/573.1 |
| 6,280,409 | B1 | * | 8/2001 | Stone et al. | 604/67 |
| 6,305,221 | B1 | * | 10/2001 | Hutchings | 73/488 |
| 6,478,736 | B1 | * | 11/2002 | Mault | 600/300 |

(Continued)

FOREIGN PATENT DOCUMENTS

WO    WO 02089081    11/2002

OTHER PUBLICATIONS

D J Walker et al., "A continuous patient activity monitor: validation and relation to disability" Physiological Measurement, Feb. 1997, IOP Publishing, UK vol. 18, No. 1, pp. 49-59 ISSN: 0967-3334.*

(Continued)

*Primary Examiner*—Hezron Williams
*Assistant Examiner*—Samir M Shah

(57) ABSTRACT

An activity monitor is provided that reduces the amount of power consumed during a monitoring operation.

11 Claims, 3 Drawing Sheets

U.S. PATENT DOCUMENTS

Figure 1:
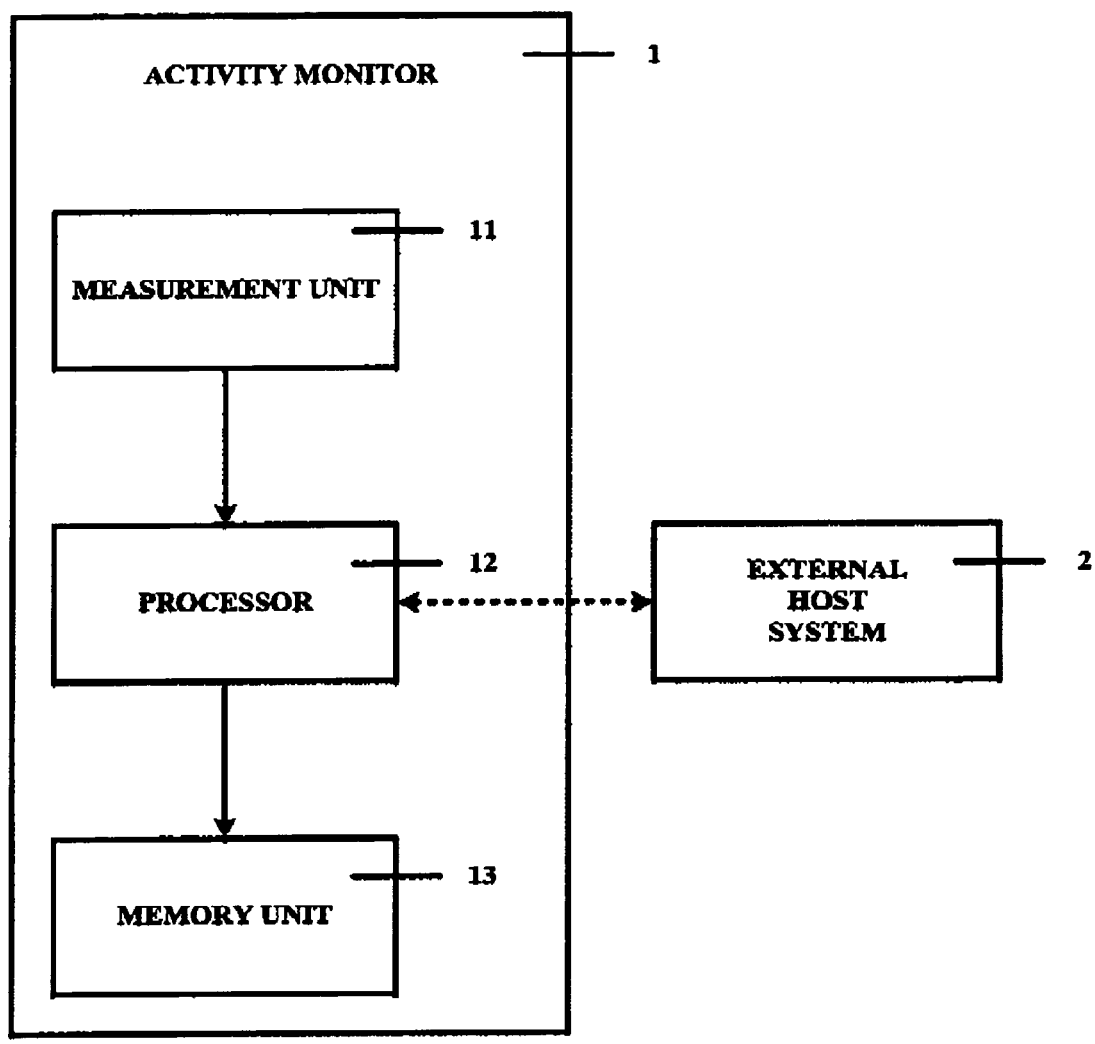

| | | | | |
|---|---|---|---|---|
| 6,826,960 | B2 * | 12/2004 | Schaad et al. | 73/514.29 |
| 6,845,670 | B1 * | 1/2005 | McNeil et al. | 73/514.32 |
| 2002/0109600 | A1 * | 8/2002 | Mault et al. | 340/573.1 |
| 2002/0116080 | A1 * | 8/2002 | Birnbach et al. | 700/66 |
| 2003/0065257 | A1 * | 4/2003 | Mault et al. | 600/407 |
| 2003/0208110 | A1 * | 11/2003 | Mault et al. | 600/300 |
| 2003/0226695 | A1 * | 12/2003 | Mault | 177/25.16 |
| 2005/0223799 | A1 * | 10/2005 | Murphy | 73/510 |
| 2006/0255955 | A1 * | 11/2006 | O'Connor et al. | 340/573.1 |

OTHER PUBLICATIONS

"Answers.com", discrete: Definition, Synonyms and Much More from Answers.com\http://www.answers.com/topic/discrete.*

Cliff Randell and Henk Muller, "Context Awareness by Analysing Accelerometer Data", Department of Computer Sciences, University of Bristor, UK, 2000.*

C. Randell et al; "Context Awareness by Analysing Accelerometer Data", Wearable Computers, The 4th Intnl Symosium on Atlanta,GA, Oct. 16, 2000, pp. 175-176 XP010526011.

Bouten et al; "A Triaxial Accelerometer and Portable Data Processing Unit for the Assessment of Daily Physical Activity", IEEE Transactions on Biomedical Engineering, vol. 44, No. 3, Mar. 1997.

* cited by examiner

ACTIVITY MONITORING

The present invention relates to activity monitoring, and in particular, but not exclusively to, activity monitoring of a human being.

The physical activity of a human being is an important determinant of its health. The amount of daily physical activity is considered to be a central factor in the etiology, prevention and treatment of various diseases. Information about personal physical activity can assist the individual in maintaining or improving his or her functional health status and quality of life.

A known system for monitoring human activity is described in the article "A Triaxial Accelerometer and Portable Data Processing Unit for the Assessment of Daily Physical Activity", by Bouten et al., IEEE Transactions on Biomedical Engineering, Vol. 44, NO. 3, March 1997.

According to the known system a triaxial accelerometer composed of three orthogonally mounted uniaxial piezoresistive accelerometers is used to measure accelerations covering the amplitude and frequency ranges of human body acceleration. An individual wears the triaxial accelerometer over a certain period of time. A data processing unit is attached to the triaxial accelerometer and programmed to determine the time integrals of the moduli of accelerometer output from the three orthogonal measurement directions. These time integrals are summed up and the output is stored in a memory that can be read out by a computer. The output of the triaxial accelerometer bears some relation to energy expenditure due to physical activity and provides as such a measure for the latter.

The known system allows for measurement of human body acceleration in three directions. Using state of the art techniques in the field of integrated circuit technology the accelerometer can be built small and lightweight allowing it to be worn for several days or even longer without imposing a burden to the individual wearing it.

However, the known system has the considerable drawback that continuous monitoring of the accelerometer signals results in relatively high power consumption. High power consumption means that large and expensive batteries are required for a practical period of operation of the activity monitor.

It is therefore desirable to provide an activity monitor that can overcome these disadvantages.

According to one aspect of the present invention, there is provided an activity monitor comprising a measurement unit including a plurality of motion sensors operable to produce respective sensor signals indicative of motion experienced thereby, and a processor operable to receive the sensor signals from the measurement unit and to process the sensor signals in accordance with a predetermined method, characterized in that the activity monitor is operable to monitor and process the sensor signals discontinuously.

Figure 2:
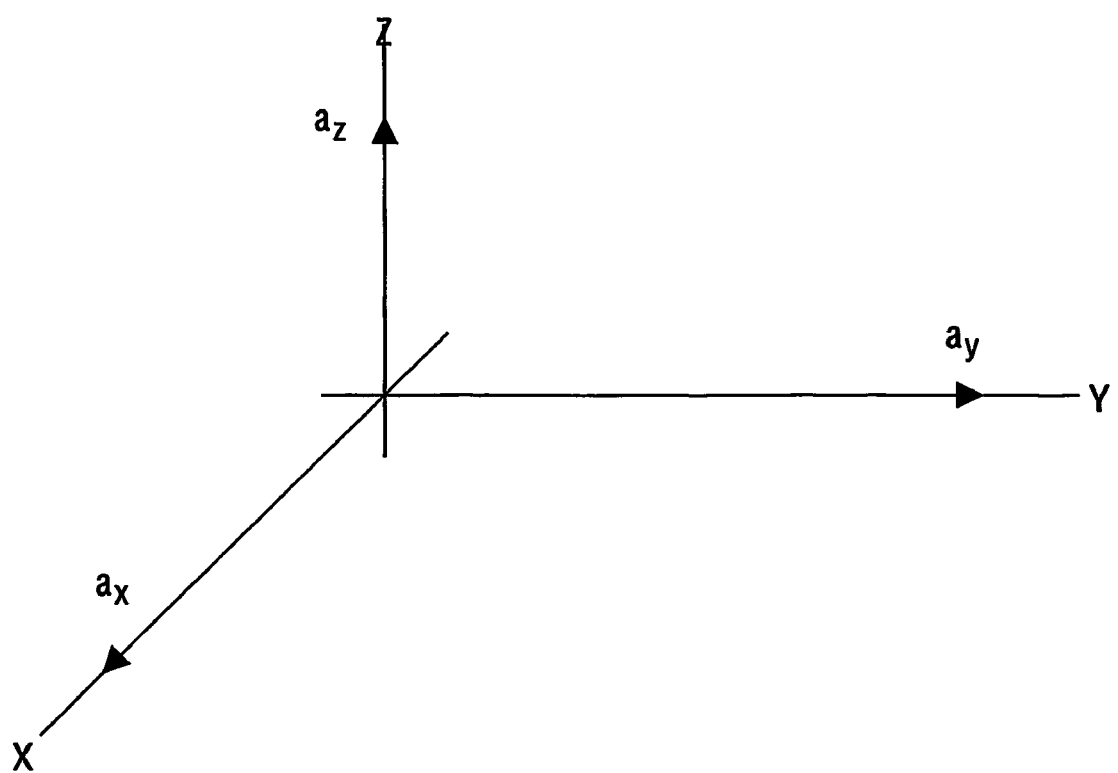

FIG. 1 shows a block diagram schematically showing the components of a system embodying one aspect of the present invention;

FIG. 2 schematically shows the orthogonal position of three accelerometers; and

Figure 3:
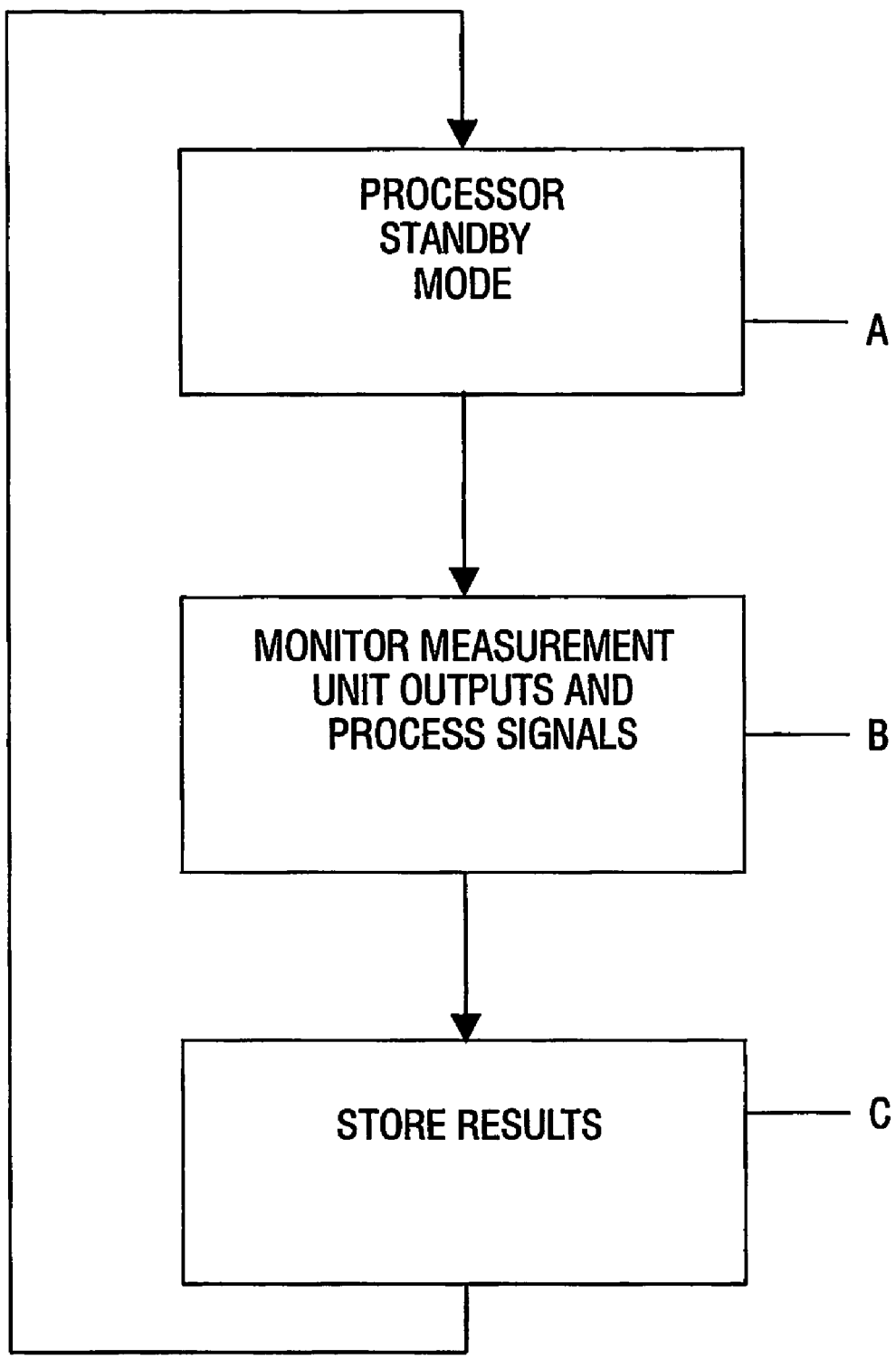

FIG. 3 shows a flow diagram of the steps of a method embodying another aspect of the present invention.

FIG. 1 illustrates an activity monitor 1 embodying one aspect of the present invention. The activity monitor 1 comprises a measurement unit 11, a processor 12, and a memory unit 13. The measurement unit 11 is operable to produce data signals indicative of the motion of the activity monitor 1, and to supply those data signals to the processor 12. The processor 12 is operable to process the data signals output from the measurement unit, and is able to store the data signals, or the results of the processing in the memory unit 13. Data can be transferred between the processor and the memory unit 13. The processor 12 is also able to be connected to an external host system 2, which can be a personal computer (PC) or other appropriate systems. The external host system 2 can be used to perform additional processing of the data held in the activity monitor 1.

In use, the activity monitor 1 is attached to the object to be monitored. For purposes of illustration in the following it is assumed that the object is a human individual, although it is clearly possible to apply such an activity monitor for any object. The activity monitor is attached to the individual or object for a certain time period.

The measurement unit comprises three accelerometers, which are arranged in mutually orthogonal directions. The accelerometers output data signals, which are indicative of the respective accelerations experienced by the accelerometers. The three accelerometers are arranged orthogonal to one another in a conventional manner.

On an individual, these directions are formed "antero-posterior", "medio-lateral" and "vertical", that are denoted as x, y and z, respectively. The accelerometers comprise strips of piezo-electric material that is uni-axial and serial bimorph. The strips are fixed at one end thereof.

The piezo-electric accelerometers act as damped mass-spring systems, wherein the piezo-electric strips act as spring and damper. Movements of the strips due to movement of the individual generate an electric charge leading to a measurement of a data signal. In case of human movements the frequency of the data signals lies in the range of 0.1-20 Hz. The amplitude of the data signals lies between −12 g and +12 g. These numbers are discussed in more detail in the article mentioned earlier. Suitable piezo-electric materials to measure such data signals are known to a person skilled in the art.

FIG. 2 illustrates the orthogonal output of the three accelerometers of the measurement unit 11. The outputs are termed $a_x$, $a_y$ and $a_z$ respectively in accordance with the present invention, and as illustrated in FIG. 3, the activity monitor operates such that the processor remains in a standby mode (step A) for a predefined period of time then inputs the measurement unit outputs and processes those signals (step B), storing the results (step C), in the memory unit 13, before returning to the standby mode.

Thus, the monitoring of the measurement unit outputs is performed in a discontinuous manner over time.

In many cases the use of the activity monitor is to find out about a total activity for a human being over a longer period of time, for example 24 hours. For this purpose, human activity normally will be monitored continuously in the frequency range of 1 to 8 Hz. This requires a sample frequency of at least 16 Hz. However, as a human person seldom changes the kind of activity that is being performed every few seconds, it is not necessary to do monitoring continuously. Accordingly, reduction in monitoring time to a few seconds with a variable time interval between monitoring periods, is beneficial for the power consumption of the activity monitor.

This discontinuous monitoring activity can be achieved by programming the processor unit appropriately, so that the processor goes into a standby (or sleep) mode after a few seconds of monitoring. The moment the monitoring is started up again can be dependent upon various strategies; for example, the software could detect changes in the human behaviour and adopt the switch on, switch off strategy of the activity monitor. The ratio of time monitoring to time in standby mode can also have a fixed value, or could be variable dependent upon activity levels, or required settings.

Further power reduction could be achieved by switching off the monitoring unit itself, such that the accelerometers or motion sensors are only active for a discontinuous amount of time.

It will be readily appreciated that the accelerometers are merely preferred motion sensors, and that any appropriate motion sensor could be used in an embodiment of the present invention and achieve the advantages of the present invention.

It is emphasised that the term "comprises" or "comprising" is used in this specification to specify the presence of stated features, integers, steps or components, but does not preclude the addition of one or more further features, integers, steps or components, or groups thereof.

The invention claimed is:

1. An activity monitor comprising:
   a measurement unit including a plurality of motion sensors operable to produce respective sensor signals indicative of motion experienced thereby; and
   a processor operable to receive the sensor signals from the measurement unit and to process the sensor signals in accordance with a predetermined method,
   characterized in that the activity monitor is operable to monitor and process the sensor signals discontinuously in time and the processor is operable to monitor the sensor signals in turn.

2. An activity monitor as claimed in claim 1, wherein the measurement unit is operable to output the sensor signals discontinuously in time.

3. An activity monitor as claimed in claim 1, wherein the processor is operable to monitor the sensor signals discontinuously in time.

4. An activity monitor as claimed in claim 1, wherein the processor is operable to enter a monitoring mode of operation in which the processor monitors the sensor signals and to enter a standby mode of operation in which no monitoring takes place.

5. An activity monitor as claimed in claim 4, wherein the processor is operable to enter the monitoring mode and the standby mode alternately.

6. An activity monitor as claimed in claim 5, wherein respective time periods for the monitoring and standby modes are variable.

7. An activity monitor as claimed in claim 5, wherein respective time periods for the monitoring and standby modes are fixed.

8. A method of monitoring activity using a plurality of motion sensors which are operable to produce respective sensor signals indicative of motion experienced thereby, the method comprising receiving the sensor signals and processing the sensor signals in accordance with a predetermined method, characterized in that the sensor signals are monitored and processed discontinuously in time and the sensor signals are monitored in turn.

9. A method as claimed in claim 8, comprising alternately monitoring the sensor signals and operating in a standby mode, in which no monitoring takes place, for respective time periods.

10. A method as claimed in claim 9, wherein the respective time periods are variable.

11. A method as claimed in claim 9, wherein the respective time periods are fixed.

* * * * *